United States Patent [19]

Somers et al.

[11] Patent Number: 5,773,269

[45] Date of Patent: Jun. 30, 1998

[54] FERTILE TRANSGENIC OAT PLANTS

[75] Inventors: David A. Somers, Roseville; Kimberly A. Torbert, St. Paul; Howard W. Rines, Shoreview, all of Minn.

[73] Assignees: Regents of the University of Minnesota, Minneapolis, Minn.; United States of America, Washington, D.C.

[21] Appl. No.: 690,170

[22] Filed: Jul. 26, 1996

[51] Int. Cl.$^6$ .............................. C12N 15/00; A01H 1/06; A01H 4/00

[52] U.S. Cl. .................................. 435/172.3; 435/172.1; 435/410; 435/419; 435/430; 47/58; 47/DIG. 1; 800/205; 800/250

[58] Field of Search .................................... 800/205, 200, 800/250; 475/172.3, 172.1; 47/58; 435/430, 430.1, 410, 419

[56] References Cited

U.S. PATENT DOCUMENTS

| | | | |
|---|---|---|---|
| 4,666,844 | 5/1987 | Cheng | 435/240 |
| 4,806,483 | 2/1989 | Wang | 435/240 |
| 5,187,073 | 2/1993 | Goldman et al. | 435/172.3 |
| 5,272,072 | 12/1993 | Kaneko et al. | 435/172.3 |
| 5,464,765 | 11/1995 | Coffee et al. | 435/172.3 |
| 5,591,616 | 1/1997 | Hiei et al. | 435/172.3 |

FOREIGN PATENT DOCUMENTS

| | | |
|---|---|---|
| WO88/09374 | 12/1988 | WIPO . |
| WO94/13822 | 6/1994 | WIPO . |
| WO95/06127 | 3/1995 | WIPO . |
| WO96/22015 | 7/1996 | WIPO . |

OTHER PUBLICATIONS

Penza, R., et al., "Gene transfer by cocultivation of Mature Embroys with *Agrobacterium tumefaciens*: application to Cowpea (Vigna unguiculata Walp)", *J. Plant Physol.*, Vo. 138, pp. 39–43, (1991).

Sathish, P., et al., "Cloning And Anti–Sense RNA Constructs of a Starch Branching Enzyme Gene From Barley Endosperm", *Photosynthesis: From Light to Biosphere, Proc. Int. Photosynth. Congr. 10th*, vol. 5—XP002048646, 313–316, (1995).

Somers, D.A., et al., "Genetic Transformation in *Avena sativa* L. (Oat)", *Biotechnological and Agricultural Forum*, vol. 38, pp. 178–190, (1996).

Carter et al. "Tissue Culture of Oats" Nature vol. 214, pp. 1029–1030, Mar. 6, 1967.

Klein et al. "Regulation of anthocyanin biosynthetic genes introduced into intact maize tissues by microprojectiles" PNAS vol. 86 pp. 6681–6685, Sep. 1989.

Potrykus, Ingo. "Gene transfer to Cereals: An Assessment." Bio/Technology pp. 535–542, Jun. 1990.

Chen, Z., et al., "Oat Leaf Base: Tissue with an Efficient Regeneration Capacity", *Plant Cell Reports (1995) 14:354 358*, Department of Plant Physiology, Botanical Institute, University of Goteburg, Carl Skottsbergs Gata 22. S–413 19 Goteborg, Sweden, 354–358, (May 27, 1994).

Chen, H., et al., "Efficient Callus Formation and Plant Regeneration From Leaves of Oats (*Avena sativa* L.)", *Plant Cell Reports (1995) 14:393 397*, Plant Microbe Interactions Group, Research School of Biological Sciences, Institute of Advanced Studies, Australian National University, Canberra, ACT 0200 Australia, 393–397, (Jul. 1, 1994).

P. Bregitzer, et al., "Development and Characterization of Friable, Embryogenic Oat Callus", *Crop Sci.*, 29, 798–803 (1989).

P. P. Bregitzer, et al., "Somatic Embryogenesis in Oat (*Avena sativa* L.)", In: *Somatic Embryogenesis and Synthetic Seed II*, Y. P. S. Bajaj, (ed.), Springer–Verlag, Berlin, pp. 53–62 (1995).

D. P. Cummings, et al., "Callus Induction Plant Regeneration in Oat" *Crop Sci.*, 16, 465–470 (1976).

J. W. Heyser, et al., "Long Term Plant Regeneration, Somatic Embryogenesis and Green Spot Formation in Secondary Oat (*Avena sativa* ) Callus", *Z. Pflanzenphysiol. Bd.*, 107, 153–160 (1982).

K. J. Scott, "Genetic Engineering of Cereals for Resistance to Phytopathogens", *Australasian Plant Pathol.*, 23, 154–162 (1994).

D. A. Somers, et al., "Fertile, Transgenic Oat Plants", *Bio/Technology*, 10, 1589–1594 (Dec., 1992).

D. A. Somers, et al., "Genetic Engineering of Oats", In: *Improvement of Cereal Quality by Genetic Engineering*, R. J. Henry et al., (eds.), Plenum Press, New York, pp. 37–45 (1994).

K. A. Torbert, et al., "Use of Paromomycin as a Selective Agent for Oat Transformation", *Plant Cell Reports, 14*, 635–640 (1995).

*Primary Examiner*—Gary Benzion
*Attorney, Agent, or Firm*—Schwegman, Lundberg, Woessner & Kluth, P.A.

[57] ABSTRACT

A method to prepare fertile transgenic oat plants by transforming cells of, or derived from, mature embryos is provided, as well as plants prepared by said method.

15 Claims, No Drawings

FERTILE TRANSGENIC OAT PLANTS

BACKGROUND OF THE INVENTION

Regeneration of fertile oat plants (*Avena sativa* L.) from cultured callus tissues was first reported in 1976 (Cummings et al., *Crop Sci.*, 16, 465 (1976)). In the 1980's, protoplast culture systems were pursued by a number of researchers to develop other regenerable oat tissue culture systems. However, these systems were not developed to the point where fertile plants could be routinely regenerated and it became apparent that regenerable oat callus or suspension culture cells were the most appropriate source of totipotent target cells for plant transformation and regeneration.

Establishment of friable, embryogenic oat callus is dependent on the source of the explant, its physiological stage and genotype, and the composition of the culture initiation medium. Current genetic engineering systems for oats use friable, embryogenic callus initiated from immature embryos, germinated seedlings, mature seed and basal sections of immature leaves as a totipotent tissue source. While tissue explants can be derived from a variety of plant sources with totipotent potential, in general, immature embryos provide the highest and most reproducible callus initiation frequency. Moreover, certain oat genotypes, such as GAF and GAF/Park, have been bred and selected for their ability to initiate callus cultures and to regenerate plants from those cultures.

To initiate callus, explants from immature embryos of the GAF genotype are cultured on MS medium containing 2 mg/l 2,4-dichlorophenoxy acetic acid (2,4-D). Friable, embryogenic sectors are visually selected from the initially produced callus and are continually selected upon subculture for development of uniformly friable, embryogenic callus. Production of sufficient callus to initiate microprojectile transformation experiments usually takes at least 3 months of selective subculturing. These cultures are routinely propagated for up to two years before being discarded. Plant regeneration is initiated on MS medium containing 2 mg/l α-naphthaleneacetic acid (NAA) and 0.2 mg/l benzylamino purine (BAP). This medium favors shoot primordia formation and proliferation. Shoots are subsequently rooted on MS medium without phytohormones.

The first report of the preparation of fertile transgenic oat plants was in 1992. Somers et al. (*Bio/technol.*, 10, 1589 (1992)) employed microprojectile bombardment to introduce the bar gene into callus cultures derived from immature embryos of the GAF/Park genotype. The bar gene encodes phosphinothricin acetyl transferase (PAT), an enzyme which confers tolerance to the herbicide phosphinothricin (PPT). The age of the callus cultures ranged from 180 days to over 365 days old. After PPT selection, Somers et al. found an overall recovery of 1.9 transgenic tissue cultures per microprojectile bombardment. While the average regeneration frequency of PPT resistant cultures was 34%, many of the regenerated plants exhibited sterility or male sterility. Only $1/38$ regenerated plants was fertile.

Torbert et al. (*Plant Cell Reports*, 14, 635 (1995)) disclose that the microprojectile bombardment of oat callus derived from immature embryos with the T7 neomycin phosphotransferase gene (npt II) resulted in an overall recovery 3.1 transgenic tissue cultures per microprojectile bombardment. The expression of the npt II gene in plant cells confers paromomycin resistance to those cells. They also disclose that the regeneration frequency of transgenic plants from paromomycin resistant tissue cultures was 36%. It is further disclosed that fertile plant production from paromomycin resistant tissue cultures was only 19%.

Potential weakness of all plant transformation systems, including oat, which utilize tissue cultures as sources of totipotent target cells, is the undesirable recovery of tissue culture-induced genetic variation in regenerated transformed plants. It has been found that the frequency of cytogenetic variation in regenerated plants varies with genotype and increases with culture age (McCoy et al., *Can. J. Genet. Cytol.*, 24, 27 (1982); Dahleen et al., *Crop Sci.*, 31, 90 (1991); Rines et al., *Agro. Monog.*, 33, 777 (1992)). Moreover, the frequency of tissue cultures which produce fertile plants declines as culture age increases. Thus, tissue culture-induced changes undoubtedly contribute to reduced plant regeneration frequency and reduced plant fertility.

Thus, what is needed is an improved method to prepare fertile transgenic oat plants.

SUMMARY OF THE INVENTION

The present invention provides an improved method for genetically transforming oat plants (*Avena sativa* L.). Thus, the invention provides methods of selecting stable genetic transformants from transformed oat callus tissue derived from mature embryos and methods of producing fertile transgenic oat plants from said transformed oat tissue. Exemplary transformation methods include the use of microprojectile bombardment to introduce a preselected DNA segment, which encodes resistance to an agent that is normally toxic to untransformed oat cells or plants, or an otherwise phenotypically observable or detectable trait, into oat callus derived from mature embryos, or directly into mature embryos. In other aspects, the invention relates to the production of stably transformed and fertile oat plants, and gametes and offspring from the transgenic plants.

The present method provides two important advantages over transformation methods using oat callus tissue from immature embryos: 1) the use of mature seed to obtain mature embryos in the present method provides a ready source of regenerable transformable target tissue year around, without being constrained by the availability of growth chambers, greenhouse space or the field; and 2) the present method permits the use of markedly younger tissue cultures to produce transgenic plants, which increases regeneration frequency and leads to increased plant fertility. As described hereinbelow, callus derived from mature embryos, which was subjected to microprojectile bombardment, had a regeneration frequency of 51% and greater than 83% of the regenerated plants were fertile. This results in an overall production of greater than 50% transgenic tissue cultures producing fertile transgenic plants.

Thus, one embodiment of the invention is a process for producing transformed *Avena sativa* cells. The process comprises introducing into the cells of mature embryo of *Avena sativa* a recombinant DNA segment which comprises a promoter operably linked to a preselected DNA segment as to yield transformed cells. Then a transformed cell line is identified or selected. A preferred embodiment of the invention includes first establishing a regenerable embryogenic callus culture from mature embryos, and then introducing the recombinant DNA segment into the cells of the callus culture. Another preferred embodiment of the invention is a process whereby the expression of the recombinant DNA segment in the transformed cells imparts a phenotypic characteristic to the transformed cells, such as herbicide or pest resistance. Yet another preferred embodiment of the invention includes the use of callus tissue from mature embryos for transformation which is at least 7, preferably at least 27, more preferably at least 40, and even more preferably at least about 60, days old, i.e., post-explant.

As used herein, the term "recombinant DNA segment" refers to a nucleic acid, i.e., to DNA, that has been derived or isolated from any appropriate tissue source and isolated from association with other components of the cell, such as nucleic acid or protein. The DNA may be subsequently chemically altered in vitro, so that its sequence is not naturally occurring, or corresponds to naturally occurring sequences that are not positioned as they would be positioned in a genome which has not been transformed with exogenous DNA, so that it can be sequenced, replicated, and/or expressed.

A preferred recombinant DNA segment includes a preselected DNA segment, which encodes a protein or RNA transcript or a mixture thereof, that is operably linked to a promoter functional in a plant cell, such as an oat cell. The preselected DNA segment may correspond to a gene that is already present in the oat genome, or one which is not normally present in the oat genome. If the preselected DNA segment is normally present in the oat genome it may not be expressed or not highly expressed. Thus, the preselected DNA segment is introduced so as to alter the expression of the protein or RNA transcript encoded by the preselected DNA segment in the cells of the plant.

The invention also provides a process for producing a fertile transgenic *Avena sativa* plant. The process comprises introducing a recombinant DNA segment which comprises a promoter operably linked to a preselected DNA segment into the cells of a mature embryo of *Avena sativa* so as to yield transformed cells. A population of transformed cells is selected or identified and a fertile transgenic plant is regenerated therefrom. The recombinant DNA segment is transmitted through a complete sexual cycle of said transgenic plant to its progeny so that it is expressed by the progeny plants. Thus, the invention also provides a transgenic *Avena sativa* plant, and seed, other plant parts, tissue, and progeny plants derived therefrom. The transgenic *Avena sativa* plants of the invention include, but are not limited to, a transgenic T0 *Avena sativa* plant, i.e., the first plant regenerated from transformed callus, a transgenic T1 *Avena sativa* plant, i.e., the first generation progeny plant, and progeny plants derived therefrom which comprise the preselected DNA segment. A preferred embodiment of the invention includes introducing the recombinant DNA segment into cells of a regenerable embryonic callus culture derived from mature embryos. Another preferred embodiment of the invention includes the use of microprojectile bombardment to introduce the recombinant DNA segment into the cells of the callus culture. It is preferred that the callus culture to be transformed by microprojectile bombardment is at least about 0.1–3 gm, more preferably at least about 0.3–2 gm, and more preferably at least about 0.5–1 gm in weight.

Also provided is a process comprising obtaining progeny from a fertile transgenic plant obtained by the process described hereinabove.

As used herein, the term "transgenic" or "transformed" with respect to a plant cell, plant part (including seed), plant tissue or plant means a plant cell, plant part, plant tissue or plant which comprises a preselected DNA segment which is introduced into the genome of a plant cell, plant part, plant tissue or plant by transformation. That is, the genome of a transgenic plant cell, plant part, plant tissue or plant has been augmented by at least one preselected DNA segment. The term "wild type" or "nontransgenic" refers to an untransformed plant cell, plant part, plant tissue or plant, i.e., one where the genome has not been altered by the presence of the preselected DNA segment.

The transformation of the plants in accordance with the invention may be carried out in essentially any of the various methods available to those skilled in the art of plant molecular biology. These include, but are not limited to, microprojectile bombardment, microinjection, electroporation of protoplasts or cells comprising partial cell walls, silicon carbide fiber-mediated DNA transfer and Agrobacterium-mediated DNA transfer.

DETAILED DESCRIPTION OF THE INVENTION

The introduction of exogenous genes into oat plants to provide a fertile transgenic oat plant with improved agronomic properties has the potential for long term improvement in, and expansion of, agriculture world-wide. The present invention provides an improved method of genetically engineering oat plants so as to result in fertile transgenic plants, e.g., having altered agronomic or physiologic traits. Such transgenic plants, and seeds derived therefrom, can sexually transmit this trait to their progeny. Exemplary traits for genetically engineered oat plants include increased stress tolerance, pest resistance, disease resistance (e.g., bacteria, viruses and fungi), improved yields, improved food content, and improved grain composition or quality.

I. Recipient Cells

The present invention employs recipient oat cells that are susceptible to transformation and subsequent regeneration into stably transformed, fertile plants. For example, mature oat embryos, or oat callus cultures initiated from mature embryos, are susceptible recipient cells useful in the practice of the invention. A preferred susceptible recipient cell is derived from an oat genotype that has been bred and selected for its ability to produce tissue cultures which can, at a high frequency, be regenerated into fertile oat plants. A more preferred recipient cell is one which is derived from elite oat cultivars.

Cultured susceptible recipient cells are preferably grown on solid supports. Nutrients are provided to the cultures in the form of media and the environmental conditions for the cultures are controlled. Media and environmental conditions which support the growth of oat cultures are well known to the art. Different oat genotypes may exhibit different growth rates and morphologies on different media.

To provide a culture of recipient cells, mature embryos of oat are dehulled and sterilized. The embryos are incubated in sterile double distilled water overnight and then the embryos are excised and placed on solid media, scutellum side down to initiate a callus culture. A preferred solid media for initiating a callus culture is MS2D (see Torbert et al., supra).

II. DNA Sequences

Virtually any DNA composition may be used for delivery to recipient oat cells to ultimately produce fertile transgenic oat plants in accordance with the present invention. The DNA segment or gene chosen for cellular introduction will often encode a protein which can be expressed in the resultant transformed cells, such as will result in a screenable or selectable trait and/or which will impart an improved phenotype to the regenerated plant. Thus, a preselected DNA segment, in the form of vectors and plasmids, or linear DNA fragments, in some instances containing only the DNA element to be expressed in the plant, and the like, may be employed. However, this may not always be the case, and the present invention also encompasses transgenic plants incorporating non-expressed transgenes.

It is envisioned that DNA sequences which are useful in transforming plants and which are expressed in plants, and in particular corn plants, are also useful in transforming oat and can be expressed in oat. Exemplary DNA sequences are provided in Tables 1, 2 and 3 in Weising et al. (*Ann. Rev. Genet.*, 22, 421 (1988)), which is incorporated by reference herein.

In certain embodiments, it is contemplated that one may wish to employ replication-competent viral vectors in oat transformation, such as those which can be employed for corn transformation, to transfer the preselected DNA segment into oat. Such vectors include, for example, wheat dwarf virus (WDV) "shuttle" vectors, such as pW1-11 and PW1-GUS (Ugaki et al., *Nucl. Acid Res.*, 19, 391(1991)). These vectors are capable of autonomous replication in corn cells as well as *E. coli,* and as such may provide increased sensitivity for detecting DNA delivered to transgenic oat cells.

A replicating vector may also be useful for delivery of genes flanked by DNA sequences from transposable elements such as Ac, Ds, or Mu, as these elements would actively promote integration of the desired DNA and hence increase the frequency of stably transformed cells. It is also contemplated that transposable elements would be useful for introducing DNA fragments lacking elements necessary for selection and maintenance of the plasmid vector in bacteria, e.g., antibiotic resistance genes and origins of DNA replication.

DNA useful for introduction into oat cells includes that which has been derived or isolated from any source, that may be subsequently characterized as to structure, size and/or function, chemically altered, and later introduced into plants. An example of such DNA "isolated" from a source would be a useful DNA sequence that is excised or removed from said source by chemical means, e.g., by the use of restriction endonucleases, so that it can be further manipulated, e.g., separated or amplified, for use in the invention, by the methodology of genetic engineering. Recovery or isolation of a given fragment of DNA from a restriction digest can employ separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. See Lawn et al., *Nucleic Acids Res.*, 9, 6103 (1981), and Goeddel et al., *Nucleic Acids Res.*, 8, 4057 (1980). Thus, DNA is "isolated" in that it is free from at least one contaminating nucleic acid with which it is normally associated in the natural source of the RNA or DNA and is preferably substantially free of any other mammalian RNA or DNA. The phrase "free from at least one contaminating source nucleic acid with which it is normally associated" includes the case where the nucleic acid is reintroduced into the source or natural cell but is in a different chromosomal location or is otherwise flanked by nucleic acid sequences not normally found in the source cell.

An example of DNA "derived" from a source, would be a DNA sequence or segment that is identified as a useful fragment within a given organism, and which is then chemically synthesized in essentially pure form. Therefore, "recombinant or preselected DNA" includes completely synthetic DNA sequences, semi-synthetic DNA sequences, DNA sequences isolated from biological sources, and DNA sequences derived from RNA, as well as mixtures thereof.

The introduced DNA includes, but is not limited to, DNA from plant genes, and non-plant genes such as those from bacteria, yeasts, animals or viruses. Moreover, it is within the scope of the invention to isolate a preselected DNA segment from a given plant genotype, and to subsequently introduce multiple copies of the preselected DNA segment into the same genotype, e.g., to enhance production of a given gene product. The introduced DNA can include modified genes, portions of genes, or chimeric genes, including genes from the same or different oat genotype. The term "chimeric gene" or "chimeric DNA" is defined as a gene or DNA sequence or segment comprising at least two DNA sequences or segments from species which do not combine DNA under natural conditions, or which DNA sequences or segments are positioned or linked in a manner which does not normally occur in the native genome of the untransformed oat plant.

The introduced DNA used for transformation herein may be circular or linear, double-stranded or single-stranded. Generally, the DNA is in the form of chimeric DNA, such as plasmid DNA, that can also contain coding regions flanked by regulatory sequences which promote the expression of the recombinant DNA present in the resultant plant.

Generally, the introduced DNA will be relatively small, i.e., less than about 30 kb to minimize any susceptibility to physical, chemical, or enzymatic degradation which is known to increase as the size of the DNA increases. As noted above, the number of proteins, RNA transcripts or mixtures thereof which is introduced into the plant genome is preferably preselected and defined, e.g., from one to about 5–10 such products of the introduced DNA may be formed.

B. Preparation of an Expression Cassette

An expression cassette can comprise a recombinant DNA molecule containing a preselected DNA segment operably linked to a promoter functional in a plant cell, preferably an oat cell. Preferably, the expression cassette itself is chimeric, i.e., the cassette comprises DNA from at least two different species, or comprises DNA from the same species, which is linked or associated in a manner which does not occur in the "native" or wild type of the species.

1. Preferred Preselected DNA Segments

A preferred embodiment of the invention provides a method for the introduction of a preselected DNA segment into fertile oat plants, which, when the preselected DNA segment is expressed in the plant, confers a desirable agronomic property to the plant. However, the present invention is not limited in scope to preselected DNA segments which encode a desirable agronomic property, as many other preselected DNA segments which encode proteins or RNA transcripts that confer desirable characteristics to oat plants are within the scope of the invention. Such DNA segments or "genes" are disclosed, for example in Lundquist et al. (U.S. Pat. No. 5,484,956), Lundquist et al. (U.S. Pat. No. 5,508,468), and by K. Weising et al. (*Ann. Rev. Genet.*, 22, 421 (1988), see Tables 1, 2 and 3), both of which are incorporated by reference herein.

Preferred agronomic properties encoded by the preselected DNA segment include, but are not limited to, insect resistance or tolerance, disease resistance or tolerance (e.g., resistance to barley yellow dwarf virus or resistance to fungal pathogens), improved food content or increased yields. For example, genetic studies have shown that for a plant to resist infection by a particular plant pathogen, the plant must have a resistance (R) gene which interacts directly or indirectly with a single avirulence (avr) gene which is present in the genome of the pathogen. Thus, the introduction a preselected DNA segment comprising a R gene into an oat plant which lacks the R gene can confer resistance to that plant to a pathogen which expresses the corresponding avr gene.

Enhanced resistance to fungal infections may be obtained by introducing a preselected DNA segment which encodes a pathogenesis related (PR) protein into an oat plant. PR proteins are proteins which are synthesized by cereals in response to infection by some pathogenic fungi (Scott, *Australasian Plant Path.*, 23, 154 (1994)). Enhanced resistance to viral infections may be obtained by introducing a preselected DNA segment encoding a viral coat protein into an oat plant.

Moreover, it is envisioned that more than one preselected DNA segment can be introduced into an oat plant. For example, a plasmid which contains a selectable marker gene (see below) and a gene which confers resistance to a particular virus, e.g., barley yellow dwarf virus, can be introduced into regenerable oat callus.

2. Promoters

Once a preselected DNA segment is obtained and amplified, it is operably combined with a promoter to form an expression cassette. The promoter can be derived from a non-oat source, e.g., Cauliflower Mosaic Virus 35S promoter, or can be a promoter already present in the oat genotype that is the transformation target, e.g., oat 12S globulin promoter (Schub et al., *Pl. Mol. Biol.*, 26, 203 (1994)).

Most genes have regions of DNA sequence that are known as promoters and which regulate gene expression. Promoter regions are typically found in the flanking DNA sequence upstream from the coding sequence in both prokaryotic and eukaryotic cells. A promoter sequence provides for regulation of transcription of the downstream gene sequence and typically includes from about 50 to about 2,000 nucleotide base pairs. Promoter sequences also contain regulatory sequences such as enhancer sequences that can influence the level of gene expression. Some isolated promoter sequences can provide for gene expression of heterologous DNAs, that is a DNA different from the native or homologous DNA. Promoter sequences are also known to be strong or weak or inducible. A strong promoter provides for a high level of gene expression, whereas a weak promoter provides for a very low level of gene expression. An inducible promoter is a promoter that provides for turning on and off of gene expression in response to an exogenously added agent or to an environmental or developmental stimulus. Promoters can also provide for tissue specific or developmental regulation. An isolated promoter sequence that is a strong promoter for heterologous DNAs is advantageous because it provides for a sufficient level of gene expression to allow for easy detection and selection of transformed cells and provides for a high level of gene expression when desired.

The promoter in an expression cassette can provide for expression of the preselected DNA segment. The promoter can also be inducible so that gene expression can be turned on or off by an exogenously added agent. For example, a bacterial promoter such as the $P_{tac}$ promoter can be induced to varying levels of gene expression depending on the level of isothiopropylgalactoside added to the transformed bacterial cells. It may also be preferable to combine the preselected DNA segment with a promoter that provides tissue specific expression or developmentally regulated gene expression in plants.

Preferred expression cassettes for oat cells will generally include promoters which are useful to express exogenous DNAs in corn cells. For example, the AdhI promoter has been shown to be strongly expressed in callus tissue, root tips, and developing kernels in corn. Thus, it is envisioned that the AdhI promoter will also be strongly expressed in oat.

Promoters which are useful to express genes in corn include, but are not limited to, a plant promoter such as the, CaMV 35S promoter (Odell et al., *Nature,* 313, 810 (1985)), or others such as CaMV 19S (Lawton et al., *Plant Mol. Biol.,* 9, 31F (1987)), nos (Ebert et al., *PNAS USA,* 84, 5745 (1987)), Adh (Walker et al., *PNAS USA,* 84, 6624 (1987)), sucrose synthase (Yang et al., *PNAS USA,* 87, 4144 (1990)), α-tubulin, ubiquitin, actin (Wang et al., *Mol. Cell. Biol.,* 12, 3399 (1992)), cab (Sullivan et al., *Mol. Gen. Genet,* 215, 431 (1989)), PEPCase (Hudspeth et al., *Plant Mol. Biol.,* 12, 579 (1989)), or those associated with the R gene complex (Chandler et al., *The Plant Cell,* 1, 1175 (1989)). Other promoters useful in the practice of the invention are known to those of skill in the art.

Tissue-specific promoters, including but not limited to, root-cell promoters (Conkling et al., *Plant Physiol.,* 93, 1203 (1990)), and tissue-specific enhancers (Fromm et al., *The Plant Cell,* 1, 977 (1989)) are also contemplated to be particularly useful, as are inducible promoters such as water-stress-, ABA- and turgor-inducible promoters (Guerrero et al., *Plant Molecular Biology,* 15, 11–26)), and the like.

Tissue specific expression may be functionally accomplished by introducing a constitutively expressed gene (all tissues) in combination with an antisense gene that is expressed only in those tissues where the gene product is not desired. Expression of an antisense transcript of this preselected DNA segment in an oat kernel, using, for example, a zein promoter, would prevent accumulation of the gene product in seed. Hence the protein encoded by the preselected DNA would be present in all tissues except the kernel.

Alternatively, one may wish to obtain novel tissue-specific promoter sequences for use in accordance with the present invention. To achieve this, one may first isolate cDNA clones from the tissue concerned and identify those clones which are expressed specifically in that tissue, for example, using Northern blotting. Ideally, one would like to identify a gene that is not present in a high copy number, but which gene product is relatively abundant in specific tissues. The promoter and control elements of corresponding genomic clones may then be localized using the techniques of molecular biology known to those of skill in the art.

In some embodiments of the present invention expression of a preselected DNA segment in a transgenic plant will occur only in a certain time period during the development of the plant. Developmental timing is frequently correlated with tissue specific gene expression. For example, in corn expression of zein storage proteins is initiated in the endosperm about 15 days after pollination.

Ultimately, the most desirable DNA segments for introduction into an oat genome may be homologous genes or gene families which encode a desired trait (e.g., increased disease resistance) and which are introduced under the control of novel promoters or enhancers, etc., or perhaps even homologous or tissue-specific (e.g., root-, collar/sheath-, whorl-, stalk-, earshank-, kernel- or leaf-specific) promoters or control elements. Indeed, it is envisioned that a particular use of the present invention will be the targeting of a preselected DNA segment in a tissue- or organelle- or developmental-specific manner.

A preselected DNA segment can be combined with the promoter by standard methods as described in Sambrook et al., In: *Molecular Cloning: A Laboratory Manual,* Cold Spring Harbor (1989)). Briefly, the preselected DNA segment can be subcloned downstream from the promoter using restriction enzymes to ensure that the DNA is inserted in proper orientation with respect to the promoter so that the DNA can be expressed. Once the preselected DNA segment is operably linked to a promoter, the expression cassette so formed can be subcloned into a plasmid or other vectors.

3. Optional Sequences in the Expression Cassette

The expression cassette can also optionally contain other DNA sequences.

a. Marker Genes

In order to improve the ability to identify transformants, one may desire to employ a selectable or screenable marker gene as, or in addition to, the expressible preselected DNA segment. "Marker genes" are genes that impart a distinct phenotype to cells expressing the marker gene and thus allow such transformed cells to be distinguished from cells that do not have the marker. Such genes may encode either a selectable or screenable marker, depending on whether the marker confers a trait which one can 'select' for by chemical means, i.e., through the use of a selective agent (e.g., a herbicide, antibiotic, or the like), or whether it is simply a trait that one can identify through observation or testing, i.e., by 'screening' (e.g., β-glucuronidase). Of course, many examples of suitable marker genes are known to the art and can be employed in the practice of the invention.

Included within the terms selectable or screenable marker genes are also genes which encode a "secretable marker" whose secretion can be detected as a means of identifying or selecting for transformed cells. Examples include markers which encode a secretable antigen that can be identified by antibody interaction, or even secretable enzymes which can be detected by their catalytic activity. Secretable proteins fall into a number of classes, including small, diffusible proteins detectable, e.g., by ELISA; small active enzymes detectable in extracellular solution (e.g., α-amylase, β-lactamase, phosphinothricin acetyltransferase); and proteins that are inserted or trapped in the cell wall (e.g., proteins that include a leader sequence such as that found in the expression unit of extensin or tobacco PR-S).

Elements of the present disclosure are exemplified in detail through the use of particular marker genes, however in light of this disclosure, numerous other possible selectable and/or screenable marker genes will be apparent to those of skill in the art in addition to the one set forth hereinbelow. Therefore, it will be understood that the following discussion is exemplary rather than exhaustive. In light of the techniques disclosed herein and the general recombinant techniques which are known in the art, the present invention renders possible the introduction of any gene, including marker genes, into a recipient cell to generate a transformed monocot.

1. Selectable Markers

Possible selectable markers for use in connection with the present invention include, but are not limited to, a neo gene (Potrykus et al., *Mol. Gen. Genet.,* 199, 183 (1985)) which codes for kanamycin resistance and can be selected for using kanamycin, G418, and the like; the npt II gene which encodes paromomycin resistance; the hyg gene which encodes hygromycin B resistance; a bar gene which codes for bialaphos resistance; a gene which encodes an altered EPSP synthase protein (Hinchee et al., *Biotech.,* 6, 915 (1988)) thus conferring glyphosate resistance; a nitrilase gene such as bxn from *Klebsiella ozaenae* which confers resistance to bromoxynil (Stalker et al., *Science,* 242, 419 (1988)); a mutant acetolactate synthase gene (ALS) which confers resistance to imidazolinone or other ALS-inhibiting chemicals (European Patent Application 154,204, 1985); a methotrexate-resistant DHFR gene (Thillet et al., *J. Biol. Chem.,* 263, 12500 (1988)); a dalapon dehalogenase gene that confers resistance to the herbicide dalapon; or a mutated anthranilate synthase gene that confers resistance to 5-methyl tryptophan. Where a mutant EPSP synthase gene is employed, additional benefit may be realized through the incorporation of a suitable chloroplast transit peptide, CTP (European Patent Application 0,218,571, 1987). See also Table 1 of Lundquist et al. (U.S. Pat. No. 5,484,956).

An illustrative embodiment of a selectable marker gene capable of being used to select transformants is the gene that encodes the enzyme phosphinothricin acetyltransferase, such as the bar gene (see Somers et al., supra (1992)). The enzyme phosphinothricin acetyl transferase (PAT) inactivates the active ingredient in the herbicide bialaphos, phosphinothricin (PPT). PPT inhibits glutamine synthetase, (Murakami et al., *Mol. Gen. Genet.,* 205, 42 (1986); Twell et al., *Plant Physiol.,* 91, 1270 (1989)) causing rapid accumulation of ammonia and cell death.

2. Screenable Markers

Screenable markers that may be employed include, but are not limited to, a β-glucuronidase or uidA gene (GUS) which encodes an enzyme for which various chromogenic substrates are known; an R-locus gene, which encodes a product that regulates the production of anthocyanin pigments (red color) in plant tissues (Dellaporta et al., in *Chromosome Structure and Function,* pp. 263–282 (1988)); a β-lactamase gene (Sutcliffe, *PNAS USA,* 75, 3737 (1978)), which encodes an enzyme for which various chromogenic substrates are known (e.g., PADAC, a chromogenic cephalosporin); a xylE gene (Zukowsky et al., *PNAS USA,* 80, 1101 (1983)) which encodes a catechol dioxygenase that can convert chromogenic catechols; an α-amylase gene (Ikuta et al., *Biotech.,* 8, 241 (1990)); a tyrosinase gene (Katz et al., *J. Gen. Microbiol.,* 129, 2703 (1983)) which encodes an enzyme capable of oxidizing tyrosine to DOPA and dopaquinone which in turn condenses to form the easily detectable compound melanin; a β-galactosidase gene, which encodes an enzyme for which there are chromogenic substrates; a luciferase (lux) gene (Ow et al., *Science,* 234, 856 (1986)), which allows for bioluminescence detection; or even an aequorin gene (Prasher et al., *Biochem. Biophys. Res. Comm.,* 126, 1259 (1985)), which may be employed in calcium-sensitive bioluminescence detection, or a green fluorescent protein gene (Niedz et al., *Plant Cell Reports,* 14, 403 (1995)).

A further screenable marker contemplated for use in the present invention is firefly luciferase, encoded by the lux gene. The presence of the lux gene in transformed cells may be detected using, for example, X-ray film, scintillation counting, fluorescent spectrophotometry, low-light video cameras, photon counting cameras or multiwell luminometry. It is also envisioned that this system may be developed for populational screening for bioluminescence, such as on tissue culture plates, or even for whole plant screening.

b. Other Sequences

Transcription enhancers or duplications of enhancers can be used to increase expression from a particular promoter. Examples of such enhancers include, but are not limited to, elements from the CaMV 35S promoter and octopine synthase genes (Last et al., U.S. Pat. No. 5,290,924, issued Mar. 1, 1994). It is proposed that the use of an enhancer element, such as the ocs element, and particularly multiple copies of the element, will act to increase the level of transcription from adjacent promoters when applied in the context of oat transformation.

As the DNA sequence inserted between the transcription initiation site and the start of the coding sequence, i.e., the untranslated leader sequence, can influence gene expression, one can also employ a particular leader sequence. Preferred leader sequence include those which comprise sequences selected to direct optimum expression of the attached gene, i.e., to include a preferred consensus leader sequence which can increase or maintain mRNA stability and prevent inappropriate initiation of translation (Joshi, *Nucl. Acid Res.*, 15, 6643 (1987)). Such sequences are known to those of skill in the art. Sequences that are derived from genes that are highly expressed in plants, and in oat in particular, will be most preferred.

Regulatory elements such as Adh intron 1 (Callis et al., *Genes Develop.*, 1, 1183 (1987)), sucrose synthase intron (Vasil et al., *Plant Physiol.*, 91, 5175 (1989)) or TMV omega element (Gallie et al., *The Plant Cell*, 1, 301 (1989)) can also be included where desired. Other such regulatory elements useful in the practice of the invention are known to those of skill in the art.

Additionally, expression cassettes can be constructed and employed to target the gene product of the preselected DNA segment to an intracellular compartment within plant cells or to direct a protein to the extracellular environment. This can generally be achieved by joining a DNA sequence encoding a transit or signal peptide sequence to the coding sequence of the preselected DNA segment. The resultant transit, or signal, peptide will transport the protein to a particular intracellular, or extracellular destination, respectively, and can then be post-translationally removed. Transit or signal peptides act by facilitating the transport of proteins through intracellular membranes, e.g., vacuole, vesicle, plastid and mitochondrial membranes, whereas signal peptides direct proteins through the extracellular membrane. By facilitating transport of the protein into compartments inside or outside the cell, these sequences can increase the accumulation of gene product.

The preselected DNA segment can be directed to a particular organelle, such as the chloroplast rather than to the cytoplasm. Thus, the expression cassette can further comprise a chloroplast transit peptide encoding DNA sequence operably linked between a promoter and the preselected DNA segment (for a review of plastid targeting peptides, see Heijne et al., *Eur. J. Biochem.*, 180, 535 (1989); Keegstra et al., *Ann. Rev. Plant Physiol. Plant Mol. Biol.*, 40, 471 (1989)). This is exemplified by the use of the rbcS (RuBISCO) transit peptide which targets proteins specifically to plastids. For example, see Glassman et al., U.S. Pat. No. 5,258,300.

It may be useful to target DNA itself within a cell. For example, it may be useful to target an introduced preselected DNA to the nucleus as this may increase the frequency of transformation. Within the nucleus itself, it would be useful to target a gene in order to achieve site-specific integration. For example, it would be useful to have a gene introduced through transformation replace an existing gene in the cell.

When the expression cassette is to be introduced into a plant cell, the expression cassette can also optionally include 3' nontranslated plant regulatory DNA sequences that act as a signal to terminate transcription and allow for the polyadenylation of the resultant MRNA. The 3' nontranslated regulatory DNA sequence preferably includes from about 300 to 1,000 nucleotide base pairs and contains plant transcriptional and translational termination sequences. Preferred 3' elements are derived from those from the nopaline synthase gene of *Agrobacterium tumefaciens* (Bevan et al., *Nucl. Acid Res.*, 11, 369 (1983)), the terminator for the T7 transcript from the octopine synthase gene of *Agrobacterium tumefaciens,* and the 3' end of the protease inhibitor I or II genes from potato or tomato, although other 3' elements known to those of skill in the art can also be employed. These 3' nontranslated regulatory sequences can be obtained as described in An, *Methods in Enxymology,* 153, 292 (1987) or are already present in plasmids available from commercial sources such as Clontech, Palo Alto, Calif. The 3' nontranslated regulatory sequences can be operably linked to the 3' terminus of the preselected DNA segment.

An expression cassette can also be introduced into an expression vector, such as a plasmid. Plasmid vectors include additional DNA sequences that provide for easy selection, amplification, and transformation of the expression cassette in prokaryotic and eukaryotic cells, e.g., pUC-derived vectors, pSK-derived vectors, pGEM-derived vectors, pSP-derived vectors, or pBS-derived vectors. Thus, additional DNA sequences include origins of replication to provide for autonomous replication of the vector, selectable marker genes, preferably encoding antibiotic or herbicide resistance, unique multiple cloning sites providing for multiple sites to insert DNA sequences or genes encoded in the expression cassette, and sequences that enhance transformation of prokaryotic and eukaryotic cells.

Another vector that is useful for expression in both plant and prokaryotic cells is the binary Ti plasmid (as disclosed in Schilperoort et al., U.S. Pat. No. 4,940,838, issued Jul. 10, 1990) as exemplified by vector pGA582. This binary Ti plasmid vector has been previously characterized by An, cited supra, and is available from Dr. An. This binary Ti vector can be replicated in prokaryotic bacteria such as *E. coli* and Agrobacterium. The Agrobacterium plasmid vectors can be used to transfer the expression cassette to plant cells. The binary Ti vectors preferably include the nopaline T DNA right and left borders to provide for efficient plant cell transformation, a selectable marker gene, unique multiple cloning sites in the T border regions, the colE1 replication of origin and a wide host range replicon. The binary Ti vectors carrying an expression cassette of the invention can be used to transform both prokaryotic and eukaryotic cells, but is preferably used to transform plant cells.

III. DNA Delivery

The expression cassette or vector is then introduced into a recipient cell to create a transformed cell. For the introduction of an expression cassette into oat cells, the frequency of occurrence of plant cells receiving DNA is be believed to be low. Moreover, it is most likely that not all recipient cells receiving DNA segments or sequences will result in a transformed cell wherein the DNA is stably integrated into the plant genome and/or expressed. Some may show only initial and transient gene expression. However, certain cells from virtually any oat line may be stably transformed, and these cells regenerated into transgenic plants.

A preselected DNA segment may be delivered into plant cells or tissues, or prokaryotic or eukaryotic non-plant cells, by currently available methods including, but not limited to, protoplast transformation, tungsten whiskers (Coffee et al., U.S. Pat. No. 5,302,523, issued Apr. 12, 1994), directly by microorganisms with infectious plasmids, infectious viruses, the use of liposomes, microinjection by mechanical or laser beam methods, by whole chromosomes or chromosome fragments, electroporation, silicon carbide fibers, and microprojectile bombardment. A preferred embodiment of the invention accomplishes the introduction of a preselected DNA segment into oat cells by methods of transformation especially effective for oats, which include, but is not limited to, microprojectile bombardment.

Introduction and expression of foreign genes in dicotyledonous (broad-leafed) plants such as tobacco, potato and alfalfa has been shown to be possible using the T-DNA of the tumor-inducing (Ti) plasmid of *Agrobacterium tumefaciens* (See, for example, Umbeck, U.S. Pat. No. 5,004,863, and international application PCT/US93/02480). Using recombinant DNA techniques and bacterial genetics, a wide variety of foreign DNAs can be inserted into T-DNA in Agrobacterium. Following infection by the bacterium containing the recombinant Ti plasmid, the foreign DNA is inserted into the host plant chromosomes, thus producing a genetically engineered cell and eventually a genetically engineered plant. A second approach is to introduce root-inducing (Ri) plasmids as the gene vectors.

Recently, rice and corn, which are monocots, have been shown to be susceptible to transformation by Agrobacterium. However, many other important monocot crop plants including wheat, barley, oats, sorghum, millet, and rye have not yet been successfully transformed by Agrobacterium. The Ti plasmid, however, may be manipulated in the future to act as a vector for oat plants. Additionally, using the Ti plasmid as a model system, it may be possible to artificially construct transformation vectors for oat plants. Ti-plasmids might also be introduced into oats by artificial methods such as microinjection, or fusion between monocot protoplasts and bacterial spheroplasts containing the T-region, which can then be integrated into the plant nuclear DNA.

IV. Production and Characterization of Stable Transgenic Plants

After effecting delivery of a preselected DNA segment to recipient cells by any of the methods discussed above, the next steps of the invention generally concern identifying the transformed cells for further culturing and plant regeneration. As mentioned above, in order to improve the ability to identify transformants, one may desire to employ a selectable or screenable marker gene as, or in addition to, the expressible preselected DNA segment. In this case, one would then generally assay the potentially transformed cell population by exposing the cells to a selective agent or agents, or one would screen the cells for the desired marker gene trait. Then, depending on the type of plant, the level of gene expression, and the activity of the protein encoded by the preselected DNA segment, introduction of the preselected DNA into the plant can confer an identifiable phenotype to the plant.

A. Selection

An exemplary embodiment of methods for identifying transformed cells involves exposing the bombarded cultures to a selective agent, such as a metabolic inhibitor, an antibiotic, herbicide or the like as described hereinabove. Cells which have been transformed and have stably integrated a marker gene conferring resistance to the selective agent used, will grow and divide in culture. Sensitive cells will not be amenable to further culturing.

It is further contemplated that combinations of screenable and selectable markers will be useful for identification of transformed cells. In some cell or tissue types, a selection agent, such as the antibiotic paromomycin, kanamycin or G418, may either not provide enough selective killing to clearly identify transformed cells, or may cause substantial nonselective inhibition of transformants and nontransformants alike, thus causing the selection technique to fail. It is proposed that selection with a growth inhibiting compound, such as an antibiotic, at concentrations below those that cause 100% inhibition followed by screening of growing tissue for expression of a screenable marker gene, such as gus (beta-glucuronidase) or lux (luciferase), would allow one to recover transformants from cell or tissue types that are not amenable to selection alone. Therefore combinations of selection and screening can enable one to identify transformants in a wider variety of cell and tissue types.

B. Regeneration and Seed Production

Cells that survive the exposure to the selective agent, or cells that have been scored positive in a screening assay, may be cultured in media that supports regeneration of plants. The transformed cells, identified by selection or screening and cultured in an appropriate medium that supports regeneration, will then be allowed to regenerate into mature plants. After the plants have reached the stage of shoot and root development, they may be transferred to a growth chamber or greenhouse for further growth and testing.

Mature plants are then obtained from cell lines that are identified as expressing the preselected DNA segment. If possible, the regenerated plants are self pollinated. In addition, pollen obtained from the regenerated plants is crossed to seed grown plants of agronomically important oat genotypes. In some cases, pollen from plants of these oat genotypes is used to pollinate regenerated plants. The trait is genetically characterized by evaluating the segregation of the trait in first and later generation progeny. The heritability and expression in plants of traits selected in tissue culture are of particular importance if the traits are to be commercially useful.

Regenerated oat plants can be repeatedly crossed to other oat genotypes in order to introgress the preselected DNA segment into the genome of the other oat plants. This process is referred to as backcross conversion. When a sufficient number of crosses to the recurrent parent have been completed in order to produce a product of the backcross conversion process that is substantially isogenic with the recurrent parent except for the presence of the introduced preselected DNA segment, the plant is self-pollinated at least once in order to produce a homozygous backcross converted plant containing the preselected DNA segment. Progeny of these plants are true breeding.

Alternatively, seed from transformed oat plants regenerated from transformed tissue cultures is grown in the field and self-pollinated to generate true breeding plants. Progeny from these plants become true breeding lines.

Once the initial breeding lines are selected, test crosses are made and hybrid seed is produced. The testcross hybrids and breeding populations are planted in several different arrays in the field. One scheme of evaluation is to grow populations of hybrid plants containing the preselected DNA segment in many different locations and measure the performance of the plants at these different locations. Yield information as well as other measures of plant health, superiority and viability are made. The information regarding the performance of these hybrids along with that of the performance of non-transformed hybrids is compared.

Upon the identification of the superior performance of transgenic plants, the parent selections are advanced and an oat line is produced through conventional breeding techniques. Hybrid plants having one or more parents containing the preselected DNA segment are tested in commercial testing and evaluation programs and performance documented. This testing includes the evaluation of performance trials carried out over a wide geographical area, as well as the use of dedicated trials to reveal performance advantage and hence value.

An additional advantage of the expression of the preselected DNA segment is the superior performance of the parental lines in the production of hybrids.

C. Characterization

To confirm the presence of the preselected DNA segment (s) or "transgene(s)" in the regenerating plants, a variety of assays may be performed. Such assays include, for example, "molecular biological" assays well known to those of skill in the art, such as Southern and Northern blotting and PCR; "biochemical" assays, such as detecting the presence of a protein product, e.g., by immunological means (ELISAs and Western blots) or by enzymatic function; plant part assays, such as leaf or root assays; and also, by analyzing the phenotype of the whole regenerated plant.

1. DNA Integration, RNA Expression and Inheritance

Genomic DNA may be isolated from callus cell lines or any plant parts to determine the presence of the preselected DNA segment through the use of techniques well known to those skilled in the art. Note that intact sequences may not always be present, presumably due to rearrangement or deletion of sequences in the cell.

The presence of DNA elements introduced through the methods of this invention may be determined by polymerase chain reaction (PCR). Using this technique discreet fragments of DNA are amplified and detected by gel electrophoresis. This type of analysis permits one to determine whether a preselected DNA segment is present in a stable transformant, but does not prove integration of the introduced preselected DNA segment into the host cell genome. In addition, it is not possible using PCR techniques to determine whether transformants have exogenous genes introduced into different sites in the genome, i.e., whether transformants are of independent origin. It is contemplated that using PCR techniques it would be possible to clone fragments of the host genomic DNA adjacent to an introduced preselected DNA segment.

Positive proof of DNA integration into the host genome and the independent identities of transformants may be determined using the technique of Southern hybridization. Using this technique, specific DNA sequences that were introduced into the host genome and flanking host DNA sequences can be identified. Hence the Southern hybridization pattern of a given transformant serves as an identifying characteristic of that transformant. In addition, it is possible through Southern hybridization to demonstrate the presence of introduced preselected DNA segments in high molecular weight DNA, i.e., confirm that the introduced preselected DNA segment has been integrated into the host cell genome. The technique of Southern hybridization provides information that is obtained using PCR, e.g., the presence of a preselected DNA segment, but also demonstrates stable integration into the genome and characterizes each individual transformant.

It is contemplated that using the techniques of dot or slot blot hybridization which are modifications of Southern hybridization techniques one can obtain the same information that is derived from PCR, e.g., the presence of a preselected DNA segment.

Both PCR and Southern hybridization techniques can be used to demonstrate transmission of a preselected DNA segment to progeny. In most instances the characteristic Southern hybridization pattern for a given transformant will segregate in progeny as one or more Mendelian genes (Spencer et al., *Plant Mol. Biol.*, 18, 201 (1992); Laursen et al., *Plant Mol. Biol.*, 24, 51 (1994)) indicating stable inheritance of the gene.

Whereas DNA analysis techniques may be conducted using DNA isolated from any part of a plant, RNA may only be expressed in particular cells or tissue types and hence it will be necessary to prepare RNA for analysis from these tissues. PCR techniques may also be used for detection and quantitation of RNA produced from introduced preselected DNA segments. In this application of PCR it is first necessary to reverse transcribe RNA into DNA, using enzymes such as reverse transcriptase, and then through the use of conventional PCR techniques amplify the DNA. In most instances PCR techniques, while useful, will not demonstrate integrity of the RNA product. Further information about the nature of the RNA product may be obtained by Northern blotting. This technique will demonstrate the presence of an RNA species and give information about the integrity of that RNA. The presence or absence of an RNA species can also be determined using dot or slot blot Northern hybridizations. These techniques are modifications of Northern blotting and will only demonstrate the presence or absence of an RNA species.

2. Gene Expression

While Southern blotting and PCR may be used to detect the preselected DNA segment in question, they do not provide information as to whether the preselected DNA segment is being expressed. Expression may be evaluated by specifically identifying the protein products of the introduced preselected DNA segments or evaluating the phenotypic changes brought about by their expression.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focussing, or by chromatographic techniques such as ion exchange or gel exclusion chromatography. Specific antibodies may be used to detect the unique structures of proteins via formats such as an ELISA assay, for example to detect npt II. Combinations of approaches may be employed to obtain even greater specificity such as western blotting, in which antibodies are used that bind to individual gene products that have been separated by electrophoretic techniques. Additional techniques may be employed to absolutely confirm the identity of the product of interest, such as evaluation by amino acid sequencing following purification. Although these procedures are among the most commonly employed, other procedures may be additionally used.

Assay procedures may also be used to identify the expression of proteins by their functionality, especially the ability of enzymes to catalyze specific chemical reactions involving specific substrates and products. These reactions may be followed by providing and quantifying the loss of substrates or the generation of products of the reactions by physical or chemical procedures.

Very frequently the expression of a gene product is determined by evaluating the phenotypic results of its expression. These assays also may take many forms including but not limited to analyzing changes in the chemical composition, morphology, or physiological properties of the plant. Chemical composition may be altered by expression of preselected DNA segments encoding proteins which affect pigmentation of plant parts and may be detected phenotypically, or by a product, which is increased when the protein encoded by the preselected DNA segment is expressed, that may be analyzed by high performance liquid chromatography or ELISA (npt II).

D. Establishment of the Introduced DNA in Other Oat Varieties

Fertile, transgenic plants may then be used in a conventional oat breeding program in order to incorporate the preselected DNA segment into the desired lines or varieties.

Generally, the commercial value of the transformed oat produced herein will be greatest if the preselected DNA segment can be incorporated into many different hybrid combinations. A farmer typically grows several hybrids based on differences in maturity, standability, and other agronomic traits. Also, the farmer must select a hybrid based upon his or her geographic location since hybrids adapted to one region are generally not adapted to another because of differences in such traits as maturity, disease, drought and insect resistance. As such, it is necessary to incorporate the gene into a large number of parental lines so that many hybrid combinations can be produced containing the preselected DNA segment.

Oat breeding and the techniques and skills required to transfer genes from one line or variety to another are well known to those skilled in the art. Thus, introducing a preselected DNA segment, preferably in the form of recombinant DNA, into any other line or variety can be accomplished by these breeding procedures.

E. Uses of Transgenic Plants

The transgenic plants produced herein are expected to be useful for a variety of commercial and research purposes. Transgenic plants can be created for use in traditional agriculture to possess traits beneficial to the grower (e.g., agronomic traits such as resistance to water deficit, pest resistance, herbicide resistance or increased yield), beneficial to the consumer of the grain harvested from the plant (e.g., improved nutritive content in human food or animal feed), or beneficial to the food processor (e.g., improved processing traits). In such uses, the plants are generally grown for the use of their grain in human or animal foods. However, other parts of the plants, including stalks, husks, vegetative parts, and the like, may also have utility, including use as part of animal silage or for ornamental purposes. Often, chemical constituents of oat and other crops are extracted for foods or industrial use and transgenic plants may be created which have enhanced or modified levels of such components.

Transgenic plants may also find use in the commercial manufacture of proteins or other compounds, where the compound of interest is extracted or purified from plant parts, seeds, and the like. Cells or tissue from the plants may also be cultured, grown in vitro, or fermented to manufacture such molecules.

The transgenic plants may also be used in commercial breeding programs, or may be crossed or bred to plants of related crop species. Improvements encoded by the preselected DNA segment may be transferred, e.g., from oat cells to cells of other species, e.g., by protoplast fusion.

The transgenic plants may have many uses in research or breeding, including creation of new mutant plants through insertional mutagenesis, in order to identify beneficial mutants that might later be created by traditional mutation and selection. An example would be the introduction of a recombinant DNA sequence encoding a transposable element that may be used for generating genetic variation. The methods of the invention may also be used to create plants having unique "signature sequences" or other marker sequences which can be used to identify proprietary lines or varieties.

The invention will be further described by the following examples.

EXAMPLE 1

Mature oat seed of GP-1, which is a selection from the GAF/Park genotype (Bregitzer et al., Crop Sci., 29, 798 (1989)), and seed from two breeding lines, Starter-1 and MN89127 were dehulled and sterilized for 30 seconds in 95% ethanol, 5 minutes in 2.5% hypochlorite containing 1–2 drops of Tween 20, and rinsed three times in sterile double deionized water for five minutes per rinse. Sterilized seeds were placed in 50 ml sterile double deionized water and left on a shaker (145 rpm) overnight at 28° C. The next day, mature embryos were excised and placed scutellum side down on MS2D medium (Torbert et al., supra). The embryos were cultured on the same plate for 8 weeks. Shoots were excised as they appeared during the first 2–4 weeks and roots were removed after the first week.

Embryogenic appearing callus that developed after 8 weeks was employed for DNA delivery via microprojectile bombardment. Callus derived tissue was plated onto solid MS2D medium containing 0.2M sorbitol and 0.2M mannitol as an osmoticum pretreatment for 4 hours prior to microprojectile bombardment as described by Vain et al. (*Plant Cell Reports*, 12, 84 (1993)).

In general, either tungsten (1.1 micron; M-17; Biorad Laboratories, Hercules, Calif.) or gold (1.0 micrometer; Biorad Laboratories, Hercules, Calif.) particles may be employed for microparticle bombardment. Approximately 60 mg of dry tungsten or gold particles is placed in 1 ml of 100% ethanol in a microtube. The tube is vortexed on high for 1–2 minutes. The vortexing is repeated three times for 30 seconds. Then the microtube is subjected to centrifugation at 10,000 rpm for 1 minute. The supernatant is removed and 1 ml of sterile distilled water is added, the particles resuspended, centrifuged and the supernatant removed. This process is repeated once more. The particles are then resuspended in 1 ml sterile distilled water. Fifty microliters, enough for 4–8 bombardments, is aliquoted into microtubes while vortexing. Tungsten or gold aliquots are stored at −20° C.

To a single 50 microliter aliquot of particles under continuous agitation the following is added in the following order: 5 microliters of DNA (1 microgram/microliter), 50 microliters of 2.5M $CaCl_2$ and 20 microliters of 0.1M spermidine (free base, tissue culture grade, Sigma Chemical Co.). The mixture is vortexed for 3 minutes, subjected to centrifugation at 10,000 rpm for 10 seconds and the supernatant removed. The DNA coated particles are washed with 250 microliters of 100% ethanol by vortexing briefly, then subjected to centrifugation, and the supernatant removed. The particles are then resuspended in 60 microliters of 100% ethanol. 5–10 microliters of the suspension is then added to the center of the macrocarrier. The suspension is allowed to dry in a low-humidity and vibration-free environment for about 1 minute.

The cultures, approximately 0.5–1 gm in weight, were bombarded with gold particles coated with pNGI (0.625 micrograms/bombardment; Klein et al., *Plant Physiol.*, 91, 440 (1989)), which contains the nptII plant selectable marker and the β-glucuronidase ("GUS", uid4) reporter gene, using Biolistic® PDS-1000/He Particle Delivery System (BioRad Laboratories, Hercules, Calif.) operated according to the manufacturer's instructions.

Tissue remained on the osmoticum medium (MS2D plus 0.4M osmoticum) overnight and was transferred to MS2D maintenance media for 7 days at 20° C. in the dark. Transformed tissue was transferred to selection medium containing 50 mg/L paromomycin solidified with 0.35% low EEO Type I agarose (Sigma Chemical Co.) and subcultured every 2 weeks (Torbert et al., supra)). Growing colonies were isolated after about 6–8 weeks and allowed to grow for up to about 4 additional weeks. Shoots were regenerated in shoot regeneration medium (MS salts plus thiamine-HCl, 20 g/L sucrose, 2 mg/L NAA, 0.2 mg/L BAP, 50 mg/L paromomycin, pH 5.8, solidified with 0.35% low EEO Type I agarose). Roots were regenerated in root regeneration medium (MS salts plus thiamine-HCl solidified with 0.35% low EEO Type I agarose). Plants were then placed into soil and grown to maturity. Seed derived from regenerated plants was cut into cross sections and stained for GUS as described in Torbert et al. (supra). Npt II levels were determined by an NPTII ELISA assay (5'-3', Boulder, Colo.) as also described in Torbert et al. (supra).

The frequency of GP-I mature embryos that initiated embryogenic callus was more than 50% after approximately 8 weeks. Starter-i and MN89127 mature embryos exhibited 33% and 20% callus initiation frequency, respectively, but the callus initiated was primarily non-embryogenic. As it has been reported that the initiation of different genotypes can be improved by varying the media when immature embryos are used to initiate callus cultures, different media may improve the callus initiation of mature embryos of non-GAF genotypes.

Twenty-one microprojectile bombardments of mature embryo derived callus from GP-1 yielded 68 paromomycin resistant tissue cultures per bombardment, a transformation frequency that is similar to that obtained from immature embryos (Torbert et al., supra). Seventy-one percent of the transgenic callus lines from mature embryos exhibited GUS expression. Plant regeneration frequency was 51%. The fertility of regenerated plants was greater than 80%, a vast improvement over previously reported results which employed immature embryos as the source of callus tissue (Somers et al., supra; Torbert et al., supra). NPT II protein was detected in leaf tissue of plants regenerated from all 35 transgenic tissue cultures tested. Moreover, plants regenerated from 21 tissue cultures produced progeny that expressed GUS in the endosperm of the seed. Overall, the mature embryo system increased output of fertile transgenic plants over the immature embryo system.

To determine the effect of culture age on the production of transgenic cultures, callus derived from 7, 28, 56 and 63 day old explants from mature embryos was bombarded with pNGI. The highest number of transformants was obtained from tissues 8 weeks after explant (Table 1). NPT II protein was detected by ELISA in all paromomycin-resistant callus lines indicating they were transgenic. Moreover, 69% of transgenic callus lines exhibited GUS expression.

To determine the age of callus tissue which produced the highest number of fertile transgenic plants after microprojectile bombardment, transformed cultures were regenerated and the plants assayed for either GUS activity in the $T_1$ seed or NPT II protein in $T_0$ leaf material. The results show that 8 week old callus cultures yielded the highest number of fertile plants (Tables 1 and 2).

TABLE 1

| Mature Embryos | | Transgenic Cultures Produced | | |
|---|---|---|---|---|
| Age(d) | Nos. Bombarded | Nos. | Per Mature Embryo Bombarded | Per Bombardment |
| 7 | 118 | 0 | 0 | 0 |
| 28 | 120 | 5 | 0.04 | 0.42 |
| 56 | 27 | 36[a] | 1.33 | 4.00 |
| 63 | 29 | 32[a] | 1.10 | 2.67 |

[a]21 microprojectile bombardments were conducted and some embryos yielded more than one transgenic tissue culture line.

TABLE 2

| | | Nos. of Transgenic Tissue Cultures | | Tissue Cultures Producing |
|---|---|---|---|---|
| Age(d) | Total | Plant Regeneration | Fertile Plants | Fertile Transgenic Plants Per Bombardment[a] |
| 56 | 36 | 23 | 17 | 17/9 = 1.89 |
| 63 | 32 | 12 | 12 | 12/12 = 1.00 |
| Overall | 68 | 35 (51%)[b] | 29 (83%) | 29/21 = 1.38 |

[a]Plants were considered fertile and transgenic if they exhibited either GUS activity in the $T_1$ seed or NPT II protein in $T_0$ leaf material.
[b]Numbers in parentheses indicate percentages.

All publications and patents are incorporated by reference herein, as though individually incorporated by reference, as long as they are not inconsistent with the disclosure. The invention is not limited to the exact details shown and described, for it should be understood that many variations and modifications may be made while remaining within the spirit and scope of the invention defined by the claims.

What is claimed is:

1. A process for producing transformed *Avena sativa* cells comprising the steps of (i) establishing a regenerable embryogenic callus culture derived from mature embryos of *Avena sativa*, (ii) introducing into the cells of the callus culture by microprojectile bombardment, a recombinant DNA segment which comprises a promoter operably linked to a preselected DNA segment so as to yield transformed cells, and (iii) identifying or selecting a transformed cell line.

2. A process for producing a fertile transgenic *Avena sativa* plant comprising the steps of (i) introducing into the cells of a regenerable embryonic callus culture derived from mature embryos of *Avena sativa* by microprojectile bombardment, a recombinant DNA segment which comprises a promoter operably linked to a preselected DNA segment so as to yield transformed cells, (ii) identifying or selecting a population of transformed cells, and (iii) regenerating a fertile transgenic plant therefrom, wherein said recombinant DNA segment is transmitted through a complete sexual cycle of said transgenic plant to its progeny.

3. A process for producing transformed *Avena sativa* cells comprising the steps of (I) introducing into the cells of a tissue culture derived from a mature embryo by microprojectile bombardment, a recombinant DNA segment which comprises a promoter operably linked to a preselected DNA segment so as to yield transformed cells, and (ii) identifying or selecting a transformed cell line.

4. A process for producing a fertile transgenic *Avena sativa* plant comprising the steps of (I) introducing into the cells of a tissue culture derived from a mature embryo of *Avena sativa* by microprojectile bombardment, a recombinant DNA segment which comprises a promoter operably linked to a preselected DNA segment so as to yield transformed cells, (ii) identifying or selecting a population of transformed cells, and (iii) regenerating a fertile transgenic plant therefrom, wherein said recombinant DNA segment is transmitted through a complete sexual cycle of said transgenic plant to its progeny.

5. The process of claim 1, 2, 3 or 4 wherein said callus is initiated on solid media.

6. The process of claim 5 wherein said mature embryo is cultured for about 28–63 days.

7. The process of claim 1 or 3 wherein the recombinant DNA segment is expressed so as to impart a phenotypic characteristic to the transformed cells.

8. The process of claim 2 or 4 wherein the recombinant DNA segment is expressed in the fertile transgenic plant so as to impart a phenotypic characteristic to the plant.

9. The process of claim 1, 2, 3 or 4 wherein the preselected DNA segment comprises a selectable marker gene or a reporter gene.

10. A process comprising obtaining progeny from a fertile transgenic plant obtained by the process of claim 2 or 4 which comprise said DNA.

11. The process of claim 10 wherein said progeny are obtained by crossing said fertile transgenic plant with any oat genotype.

12. The process of claim 10 comprising obtaining seed from said progeny and obtaining further progeny plants comprising said DNA from said seed.

13. The process of claim 12 wherein the progeny obtained are crossed back to any oat genotype, to obtain further progeny which comprise said DNA.

14. The process of claim 13 wherein seeds are obtained from further said progeny plants and plants comprising said DNA are recovered from said seed.

15. The process of claim 13 wherein said further progeny are crossed back to any oat genotype to obtain progeny which comprise said DNA.

\* \* \* \* \*